(12) United States Patent
Clarke et al.

(10) Patent No.: US 6,636,577 B1
(45) Date of Patent: Oct. 21, 2003

(54) LASER INDUCED FLUORESCENCE WATER MEASUREMENT SYSTEM FOR NUCLEAR REACTORS

(75) Inventors: Lucas Lemar Clarke, North Canton, OH (US); Robert L. Jett, Twinsburg, OH (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/064,223

(22) Filed: Jun. 21, 2002

(51) Int. Cl.$^7$ .................................. G21C 17/022
(52) U.S. Cl. ............... 376/245; 376/248; 376/259; 376/309; 376/310; 209/579; 356/27; 356/28; 356/28.5; 356/73.1; 356/300; 356/319; 356/320; 356/371; 607/88; 607/89; 436/164; 436/172; 422/82.88; 422/82.11; 422/82.09
(58) Field of Search ................... 376/245, 248, 376/259, 309, 310; 209/579; 356/27, 28, 28.5, 73.1, 300, 319, 320, 371; 607/88, 89; 436/164, 172; 422/82.08, 82.11, 82.09

(56) References Cited

U.S. PATENT DOCUMENTS

| | | | | |
|---|---|---|---|---|
| 3,578,973 A | * | 5/1971 | Dooley et al. ............ 250/462.1 |
| 4,352,983 A | * | 10/1982 | Silvus et al. ............ 250/227.25 |
| 4,402,903 A | * | 9/1983 | Lenderking ................. 376/245 |
| 4,637,910 A | * | 1/1987 | Impink, Jr. ................... 376/216 |
| 4,690,560 A | * | 9/1987 | Coogan ........................ 356/338 |
| 4,882,122 A | * | 11/1989 | Head et al. .................. 376/245 |
| 4,892,383 A | * | 1/1990 | Klainer et al. ................. 385/12 |
| 5,059,383 A | * | 10/1991 | Modarres ..................... 376/250 |
| 5,141,312 A | * | 8/1992 | Thompson et al. .......... 356/218 |
| 5,200,615 A | * | 4/1993 | Hopenfeld .................. 250/302 |
| 5,262,644 A | * | 11/1993 | Maguire ................. 250/339.08 |
| 5,414,195 A | * | 5/1995 | Peterson et al. ................ 588/1 |
| 5,465,278 A | | 11/1995 | Cowan, II et al. ........... 376/245 |
| 5,485,270 A | * | 1/1996 | Freud et al. .................. 356/336 |
| 5,596,196 A | * | 1/1997 | Cooper et al. .......... 250/339.12 |
| 5,719,911 A | * | 2/1998 | Hettiarachchi et al. ...... 376/245 |
| 5,817,958 A | * | 10/1998 | Uchida et al. .............. 73/865.9 |
| 5,838,843 A | * | 11/1998 | Aose et al. ..................... 385/12 |
| 5,900,215 A | * | 5/1999 | Seifert et al. ............. 422/82.07 |
| 6,020,207 A | * | 2/2000 | Liu ............................. 436/164 |
| 6,040,191 A | * | 3/2000 | Grow .......................... 436/172 |
| 6,117,128 A | * | 9/2000 | Gregory ......................... 606/7 |
| 6,222,307 B1 | | 4/2001 | Roy et al. .................... 313/326 |
| 6,228,330 B1 | * | 5/2001 | Herrmann et al. ...... 422/186.05 |
| 6,514,277 B1 | * | 2/2003 | Lilge et al. .................... 607/88 |

FOREIGN PATENT DOCUMENTS

| GB | 2294539 | * | 5/1996 |
|---|---|---|---|
| JP | 0117208 | * | 9/1981 |
| JP | JO 2231597 | * | 9/1990 |

OTHER PUBLICATIONS

Amey et al, Application and development of ion chromatography for analysis of transition metal cations in the primary coolants of light water reactors, Journal of Chromatography, 640 (1993) pp. 323–333.*

(List continued on next page.)

Primary Examiner—Michael J. Carone
Assistant Examiner—John Richardson
(74) Attorney, Agent, or Firm—Armstrong Teasdale LLP

(57) ABSTRACT

A water monitoring system for a nuclear reactor is provided. In an exemplary embodiment, the water monitoring system includes a fiber optic cable having a first end and a second end, with the first end configured to optically couple to the reactor cooling water distribution system, and at least one laser light source optically coupled to the second end of the fiber optic cable. The water monitoring system also includes a spectrophotometer optically coupled to the second end of the fiber optic cable.

13 Claims, 3 Drawing Sheets

OTHER PUBLICATIONS

Paul et al, fiber Optics Reliability: Benign and Adverse Environments II, SPIE International Society for Optical Engineering, vol. 992, pp. 1 to6, Sep. 4–6, 1988, Boston, Massachusetts, USA.*

Seitz et al, Chemical Sensors based on Fiber Optics, May 1999 [wysiwyg:/243/http://www.sensormag.com/articles/0799/hot799/main.shtml].*

NTIS, DE 95613152, Applications of optical fiber to the remote fluorescence analysis, Korea cancer center hospital, Seoul, Republic of Korea, Dec. 1992.*

Brookhaven National Laboratory, 1994, "Environmental Monitoring and Measurement: Resonance Raman spectroscopy for remote sensing of chemicals".*

* cited by examiner

LASER INDUCED FLUORESCENCE WATER MEASUREMENT SYSTEM FOR NUCLEAR REACTORS

BACKGROUND OF INVENTION

This invention relates generally to nuclear reactor water measurement systems, and more particularly to laser induced fluorescence water measurement systems for nuclear reactors.

A typical boiling water reactor (BWR) includes a pressure vessel containing a nuclear fuel core immersed in circulating coolant, i.e., water, which removes heat from the nuclear fuel. The water is boiled to generate steam for driving a steam turbine-generator for generating electric power. The steam is then condensed and the water is returned to the pressure vessel in a closed loop system. Piping circuits carry steam to the turbines and carry recirculated water or feedwater back to the pressure vessel that contains the nuclear fuel.

The BWR includes several conventional closed-loop control systems that control various individual operations of the BWR in response to demands. For example a control rod drive control system (CRDCS) controls the position of the control rods within the reactor core and thereby controls the rod density within the core which determines the reactivity therein, and which in turn determines the output power of the reactor core. A recirculation flow control system (RFCS) controls core flow rate, which changes the steam/water relationship in the core and can be used to change the output power of the reactor core. These two control systems work in conjunction with each other to control, at any given point in time, the output power of the reactor core. A turbine control system (TCS) controls steam flow from the BWR to the turbine based on pressure regulation or load demand.

Boiling water nuclear reactors also contain a plurality of systems to monitor the workings of the reactor. One important system is the hydrogen water chemistry system used to mitigate stress corrosion in the reactor pressure vessel. During the process of converting water to steam in the reactor, a portion of the water may be broken down into hydrogen and oxygen ($2H_2O \rightarrow 2H_2+O_2$). The build-up of this dissolved hydrogen and oxygen is undesirable because it may contribute to the onset and acceleration of stress corrosion cracking of stainless steel piping and components in the reactor pressure vessel. The addition of hydrogen to the feed water causes a reduction in dissolved oxygen within the reactor internals and recirculation piping, and lowers the radiolytic production of hydrogen and oxygen in the vessel core region. To ensure that the hydrogen added to the feedwater is properly combined with oxygen to produce water, oxygen is added to the off-gas system upstream of the recombiners.

To ensure stoichiometric balance of hydrogen and oxygen is maintained, hydrogen water chemistry systems typically include chemical analyzers to monitor the level of dissolved hydrogen, oxygen, and other chemical species that directly or indirectly affect the corrosion potential of the reactor water. Typically, iron oxide, platinum, and stainless steel electrochemical corrosion potential (ECP) sensors are used to directly measure the corrosion potential of the water.

An iron oxide ECP sensor is used to measure corrosion potential when lower concentrations of hydrogen and higher concentrations of oxygen are in the reactor water. The sensor includes a zirconia crucible that acts as an oxygen ion transport membrane. This crucible is brazed to a metal sleeve which is in turn welded to a stainless steel mineral insulated (MI) cable. The cable carries the signal generated by the sensor to an electronic processor which then generates a readout. Inside of the zirconia crucible, a mixture of iron and iron oxide powder is compacted around an iron center wire that is connected to the center wire of the MI cable. The potential accross the wall of the zirconia crucible (membrane) changes with the changing corrosion potential which is due to changes in oxygen and hydrogen concentrations among others.

Platinum and stainless steel ECP sensors are used to measure corrosion potential when there are higher concentrations of hydrogen in the reactor water. These ECP sensors include either a platinum or a stainless steel cap that has been brazed onto a zirconia ceramic. The stainless steel cap is sometimes coated with noble metals to simulate the corrosion potential at the surface of a reactor component that has been coated with noble metals. The ceramic is brazed to a metal sleeve that is in turn welded to a stainless steel MI cable. When the caps are brazed to the ceramic, the center wire from the MI cable is also brazed to the cap so that there is electrical continuity between the cap and the center wire. The potential at the surface of the electrode cap changes with the changing corrosion potential which is due to changes in oxygen and hydrogen concentrations among others.

Because of the harsh environment in a nuclear reactor, for example high temperatures, high radiation, and immersion in water, the known iron oxide, platinum, and stainless steel ECP sensors have a high rate of failure. Because the location of many of the ECP sensors in a reactor are inaccessible during plant operation, a sensor failure results in the inability to collect data until the next scheduled plant maintenance shut down, when the sensor is replaced.

Further, the measurement obtained with known iron oxide, platinum, and stainless steel ECP sensors is a raw voltage representing the hydrogen and oxygen concentrations. These voltage measurements must be processed through a data acquisition system where calculations are performed to obtain corrosion potentials corrected to the hydrogen electrode scale. These corrected corrosion potentials are then used to estimate the electrochemical corrosion potential of the exposed material surfaces in various parts of the reactor. Because the calculations are based on a specific water flow rate and a particular flow profile, variations in the actual flow rate or flow profile of the reactor water through the sensor are not taken into account which may result in inaccurate corrosion potential data.

SUMMARY OF INVENTION

In one aspect, a water monitoring system for a nuclear reactor is provided. The reactor includes a pressure vessel, a core positioned in the pressure vessel, and a water distribution system having a water sampling port. The water monitoring system includes a fiber optic cable having a first end and a second end, with the first end configured to optically couple to the reactor cooling water distribution system, and at least one laser light source optically coupled to the second end of the fiber optic cable. The water monitoring system also includes a spectrophotometer optically coupled to the second end of the fiber optic cable.

In another aspect, a nuclear reactor is provided that includes a reactor pressure vessel, a core positioned in the pressure vessel, a water distribution system, and a water monitoring system. The water monitoring system includes a fiber optic cable having a first end and a second end, with the first end configured to optically couple to the reactor cooling water distribution system, and at least one laser light source optically coupled to the second end of the fiber optic cable. The water monitoring system also includes a spectrophotometer optically coupled to the second end of the fiber optic cable.

In another aspect, a method of monitoring the water circulating in a nuclear reactor is provided. The reactor includes a pressure vessel, a core positioned in the pressure vessel, and a water distribution system that includes a water sampling port. The method includes coupling a water monitoring system to the water distribution system of the nuclear reactor; and measuring the concentration of predetermined chemical species in the reactor water with the water monitoring system. The water monitoring system includes a fiber optic cable having a first end and a second end, with the first end configured to optically couple to the reactor cooling water distribution system, and at least one laser light source optically coupled to the second end of the fiber optic cable. The water monitoring system also includes a spectrophotometer optically coupled to the second end of the fiber optic cable.

DETAILED DESCRIPTION

Sensors for a nuclear reactor water monitoring system that utilize laser induced fluorescence and laser induced absorption spectroscopy are described in detail below. These sensors permit for the monitoring of concentrations of chemicals and elements including, but not limited to, dissolved nitrogen, dissolved hydrogen, dissolved oxygen, and metals, for example, zinc, iron, zirconium, cobalt, rhodium, and platinum, in the reactor water.

Figure 1:
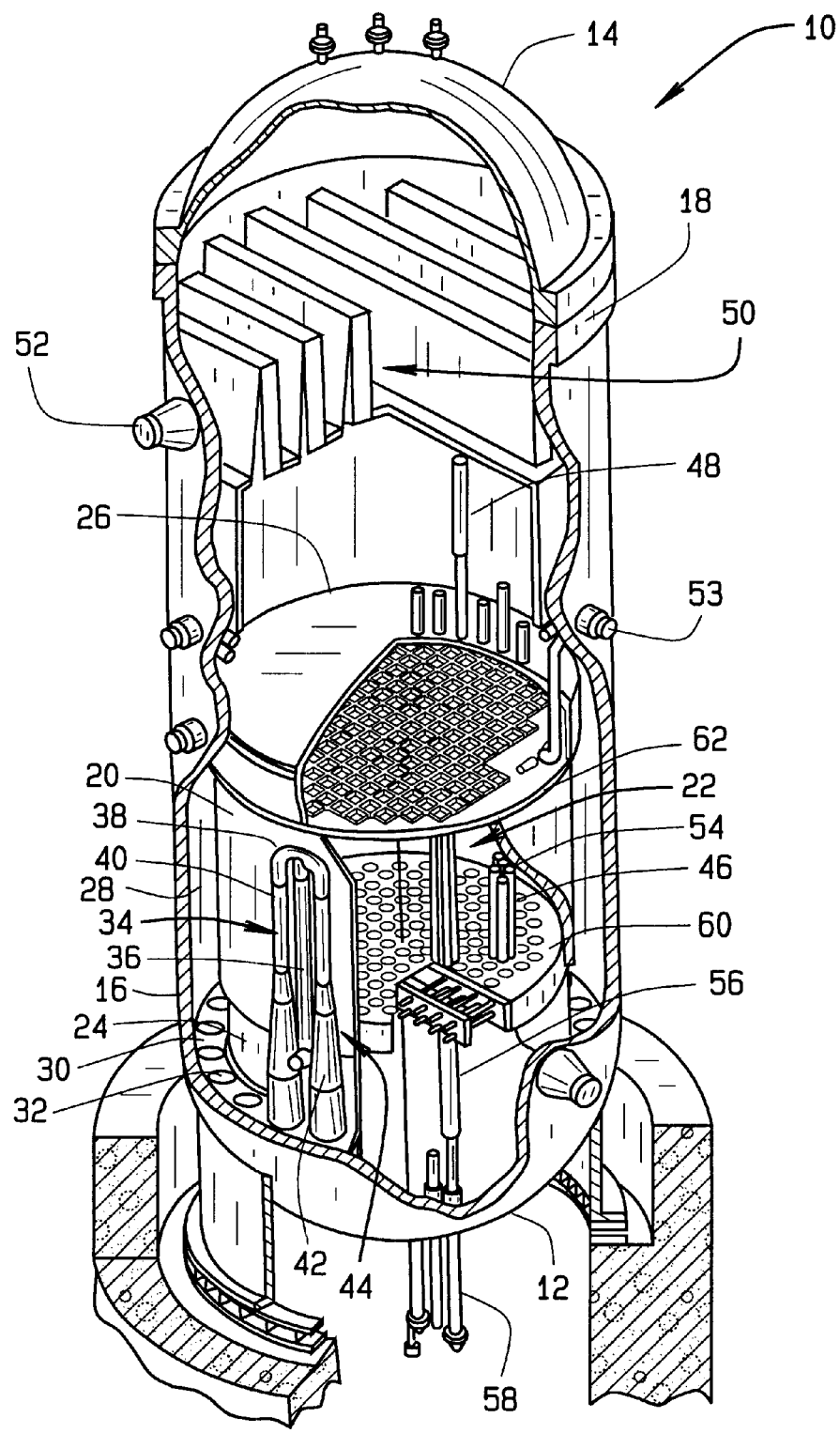
FIG. 1 is a sectional view, with parts cut away, of a boiling water nuclear reactor pressure vessel.

Referring now to the figures, FIG. 1 is a sectional view, with parts cut away, of a boiling water nuclear reactor pressure vessel (RPV) 10. RPV 10 has a generally cylindrical shape and is closed at one end by a bottom head 12 and at its other end by a removable top head 14. A side wall 16 extends from bottom head 12 to top head 14. Side wall 16 includes a top flange 18. Top head 14 is attached to top flange 18. A cylindrically shaped core shroud 20 surrounds a reactor core 22. Shroud 20 is supported at one end by a shroud support 24 and includes a removable shroud head 26 at the other end. An annulus 28 is formed between shroud 20 and side wall 16. A pump deck 30, which has a ring shape, extends between shroud support 24 and RPV side wall 16. Pump deck 30 includes a plurality of circular openings 32, with each opening housing a jet pump 34. Jet pumps 34 are circumferentially distributed around core shroud 20. An inlet riser pipe 36 is coupled to two jet pumps 34 by a transition assembly 38. Each jet pump 34 includes an inlet mixer 40, and a diffuser 42. Inlet riser 36 and two connected jet pumps 34 form a jet pump assembly 44.

Heat is generated within core 22, which includes fuel bundles 46 of fissionable material. Water circulated up through core 22 is at least partially converted to steam. Separators 48 separates steam from water, which is recirculated. Residual water is removed from the steam by steam dryers 50. The steam exits RPV 10 through a steam outlet 52 near vessel top head 14 and feed-water enters RPV through feed-water inlet 53.

The amount of heat generated in core 22 is regulated by inserting and withdrawing control rods 54 of neutron absorbing material, such as for example, hafnium. To the extent that control rod 54 is inserted into fuel bundle 46, it absorbs neutrons that would otherwise be available to promote the chain reaction which generates heat in core 22. Control rod guide tubes 56 maintain the vertical motion of control rods 54 during insertion and withdrawal. Control rod drives 58 effect the insertion and withdrawal of control rods 54. Control rod drives 58 extend through bottom head 12.

Fuel bundles 46 are aligned by a core plate 60 located at the base of core 22. A top guide 62 aligns fuel bundles 46 as they are lowered into core 22. Core plate 60 and top guide 62 are supported by core shroud 20.

Figure 2:
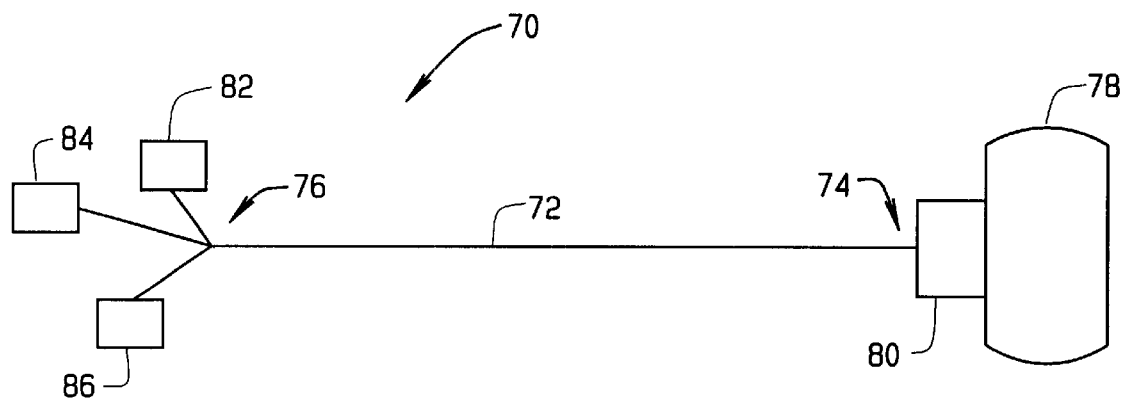
FIG. 2 is a schematic block diagram of a water monitoring system in accordance with an embodiment of the present invention.

FIG. 2 is a schematic block diagram of a water monitoring system 70 in accordance with an embodiment of the present invention. Water monitoring system 70 includes a fiber optic cable 72 having a first end 74 and a second end 76. First end 74 of fiber optic cable 72 is optically coupled to a water distribution system 78 of reactor pressure vessel 10 through a water sampling port 80. Water distribution system 78 includes the pumps, circulation piping, and any reactor component that facilitates circulation of the feed-water through reactor core 22 and the circulation of the produced steam through the steam turbines (not shown) of a power generation plant. For example, in an exemplary embodiment, water distribution system 78 includes inlet riser pipes 36, jet pumps 34, feed-water inlet 53, steam outlet 52, and shroud 20. Water distribution system 78 can also include the core spray spargers, core spray header pipes, and core spray downcomer pipes.

Second end 76 of fiber optic cable 72 is optically coupled to laser light sources 82 and 84, and to a spectrophotometer 86. Laser light sources 82 and 84 each emit a laser light beam at a wavelength suitable to cause a fluorescent or a phosphorescent emission from at least one the plurality of chemical species present in the reactor water. Laser light source 82 emits a laser beam of a different wavelength than the laser beam emitted from laser light source 84. By having light sources that emit different wavelengths of light, chemical species that do not produce a fluorescent or a phosphorescent emission at a wavelength produced by light source 82 can be monitored if light source 84 is selected to emit a laser beam at a wavelength that produces a fluorescent or a phosphorescent emission in those chemical species. In alternate embodiments, more than two laser light sources can be present in monitoring system 70, or only one laser light source can be present. Some chemical species that can be monitored and measured by system 70 include, but are not limited to, oxygen, hydrogen, nitrogen, zinc, iron, zirconium, cobalt, platinum, rhodium, carbon monoxide, hydrocarbon compounds, and the like.

Figure 3:
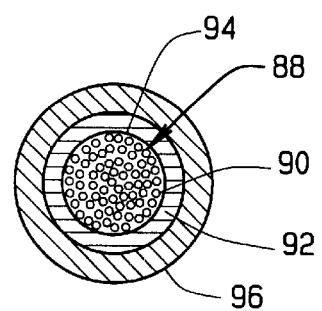
FIG. 3 is a sectional view of the fiber optic cable shown in FIG. 2.

FIG. 3 is a sectional view of fiber optic cable 72. Fiber optic cable 72 is formed from a bundle 88 of optic fibers 90. A metal coating 92 is located on an outer surface 94 of bundle 88 of optic fibers 90, and a metal housing 96 encloses bundle 88 of optic fibers 90.

Figure 4:
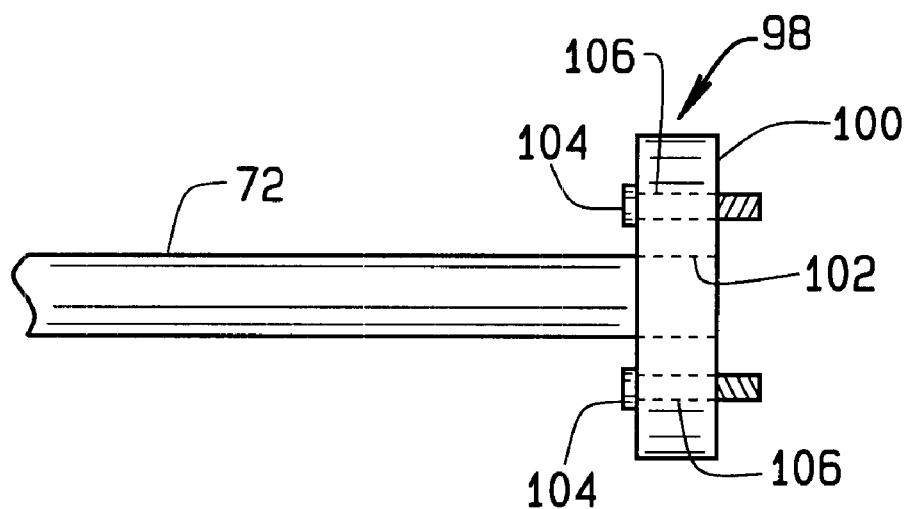
FIG. 4 is a side view of a fiber optic cable coupling assembly in accordance with an embodiment of the present invention.

FIG. 4 is a side view of a coupling assembly 98 attached to first end 74 of fiber optic cable 72. Coupling assembly 98 includes a flange portion 100 that is configured to mate with water sampling port 80 (shown in FIG. 2). A bore 102 extends through flange 100 and is sized to receive cable 72. A plurality of threaded flange bolts 104 (two shown) extend through flange bolt openings 106 in flange portion 100. Flange bolts 104 are sized to threadedly engage openings (not shown) in sampling port 80 to connect cable 72 to sampling port 80.

Figure 5:
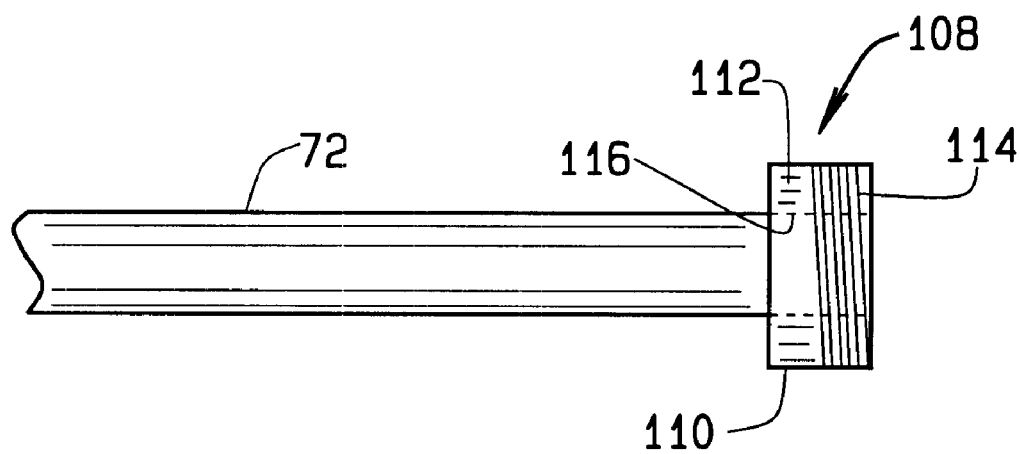
FIG. 5 is a side view of a fiber optic cable coupling assembly in accordance with another embodiment of the present invention.

FIG. 5 is a side view of a coupling assembly 108 attached to first end 74 of fiber optic cable 72, in accordance with another embodiment. Coupling assembly includes a body portion 110. An external surface 112 of body portion 110 includes threads 114. A bore 116 extends through body portion 110 and is sized to receive cable 72. Body portion 110 and threads 114 are sized and configured to threadedly engage an opening (not shown) in sampling port 80 to connect cable 72 to sampling port 80. Of course, in other embodiments, the coupling assembly can be attached to sampling port 80 by other methods, for example, the coupling assembly can include an attachment member having threads on an inner surface that maters with a threaded nipple on the sampling port to attach cable 72 to sampling port 80.

In operation, fiber optic cable 72 is optically coupled to water distribution system 78 by securing coupling assembly 98 to sampling port 80. A laser light pulse is generated by laser light source 82 having a wavelength suitable to cause a fluorescent or phosphorescent emission in the predetermined chemical species that are to be measured. For chemical species that do not produce a fluorescent or phosphorescent emission at the wavelength produced by light source 82, light source 84 can be used. The laser light pulse is transmitted through fiber optic cable 72 to water sampling port 80. The fluorescent or phosphorescent emissions produced by the laser light source are transmitted through fiber optic cable to spectrophotometer 86. Spectrophotometer 86 produces a signal corresponding to each wavelength of the fluorescent or phosphorescent emission generated by each chemical species being monitored. The intensity of the signal generated by spectrophotometer 86 for each fluorescent or phosphorescent emission generated directly corresponds to the concentration of that chemical species present in the reactor water.

While the invention has been described in terms of various specific embodiments, those skilled in the art will recognize that the invention can be practiced with modification within the spirit and scope of the claims.

What is claimed is:

1. A water monitoring system for a nuclear reactor, the reactor comprising a pressure vessel, a core positioned in the pressure vessel, reactor coolant water, and a water distribution system, said water monitoring system comprising:

a water distribution system water sampling port;

a fiber optic cable having a first end and a second end, said first end optically coupled to said water distribution system water sampling port;

at least one laser light source optically coupled to said second end of said fiber optic cable, each said laser light source configured to emit a laser light beam at a wavelength that causes a fluorescent or a phosphorescent emission from at least one predetermined chemical species present in the reactor water;

a spectrophotometer optically coupled to said second end of said fiber optic cable; and a water sampling port coupling assembly attached to said first end of said fiber optic cable, said water sampling port coupling assembly attachable to said water sampling port.

2. A water monitoring system in accordance with claim 1 wherein said fiber optic cable comprises:

a bundle of optic fibers;

a metal coating located on an outer surface of said bundle of optic fibers; and a metal housing enclosing said bundle of optic fibers.

3. A water monitoring system in accordance with claim 1 wherein each said laser light source is configured to emit a laser light beam at a wavelength that causes a fluorescent or a phosphorescent emission in at least one of oxygen, hydrogen, nitrogen, zinc, iron, zirconium, cobalt, platinum, rhodium, carbon monoxide, and hydrocarbon compounds.

4. A water monitoring system in accordance with claim 1 wherein said spectrophotometer is configured to produce a signal at a wavelength for each chemical species detected.

5. A water monitoring system in accordance with claim 4 wherein an intensity of each signal produced by said spectrophotometer is in proportion to a concentration of the detected chemical species.

6. A water monitoring system in accordance with claim 1 comprising at least two laser light sources, each said laser light source configured to emit a laser light beam of a different wavelength than other laser light sources in said water monitoring system.

7. A nuclear reactor comprising:

a reactor pressure vessel;

a core positioned in said pressure vessel;

a water distribution system comprising reactor coolant water; and a water monitoring system comprising:
- a fiber optic cable having a first end and a second end, said first end optically coupled to said reactor water distribution system;
- at least one laser light source optically coupled to said second end of said fiber optic cable, each said laser light source configured to emit a laser light beam at a wavelength that causes a fluorescent or a phosphorescent emission from at least one predetermined chemical species present in the reactor water; and
- a spectrophotometer optically coupled to said second end of said fiber optic cable.

8. A nuclear reactor in accordance with claim 7 wherein said fiber optic cable comprises:
- a bundle of optic fibers;
- a metal coating located on an outer surface of said bundle of optic fibers; and
- a metal housing enclosing said bundle of optic fibers.

9. A nuclear reactor in accordance with claim 7 wherein said water monitoring system further comprises a coupling assembly attached to said first end of said fiber optic cable, said coupling assembly coupled to a water sampling port of said water distribution system.

10. A nuclear reactor in accordance with claim 7 wherein each said laser light source is configured to emit a laser light beam at a wavelength that causes a fluorescent or a phosphorescent emission in at least one of oxygen, hydrogen, nitrogen, zinc, iron, zirconium, cobalt, platinum, rhodium, carbon monoxide, and hydrocarbon compounds.

11. A nuclear reactor in accordance with claim 7 wherein said spectrophotometer is configured to produce a signal at a wavelength for each chemical species detected.

12. A nuclear reactor in accordance with claim 11 wherein an intensity of each signal produced by said spectrophotometer is in proportion to a concentration of the detected chemical species.

13. A nuclear reactor in accordance with claim 7 wherein said water monitoring system comprises at least two laser light sources, each said laser light source configured to emit a laser light beam of a different wavelength than other laser light sources in said water monitoring system.

* * * * *